(12) United States Patent
Mahuran et al.

(10) Patent No.: US 9,415,025 B2
(45) Date of Patent: *Aug. 16, 2016

(54) METHODS OF TREATING PARKINSON'S DISEASE

(71) Applicants: The Hospital for Sick Children, Toronto (CA); McMaster University, Hamilton (CA)

(72) Inventors: Don J. Mahuran, Toronto (CA); Michael B. Tropak, Toronto (CA); Justin D. Buttner, Rosehill (AU); Jan E. Blanchard, St. Catherines (CA); Eric D. Brown, Oakville (CA)

(73) Assignees: The Hospital for Sick Children, Toronto (CA); McMaster University, Hamilton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,251

(22) Filed: Dec. 21, 2015

(65) Prior Publication Data

US 2016/0113892 A1 Apr. 28, 2016

Related U.S. Application Data

(60) Continuation of application No. 14/255,324, filed on Apr. 17, 2014, now Pat. No. 9,233,083, which is a continuation of application No. 13/676,506, filed on Nov. 14, 2012, now Pat. No. 8,951,994, which is a division of application No. 13/248,434, filed on Sep. 29, 2011, now Pat. No. 8,404,668, which is a division of application No. 12/229,445, filed on Aug. 22, 2008, now Pat. No. 8,124,597.

(60) Provisional application No. 60/972,968, filed on Sep. 17, 2007, provisional application No. 61/065,550, filed on Feb. 12, 2008, provisional application No. 61/065,684, filed on Feb. 13, 2008.

(51) Int. Cl.
| | | |
|---|---|---|
| *A61K 31/58* | (2006.01) | |
| *A61K 31/56* | (2006.01) | |
| *A61K 31/553* | (2006.01) | |
| *A61K 31/54* | (2006.01) | |
| *A61K 31/137* | (2006.01) | |

(52) U.S. Cl.
CPC .................. *A61K 31/137* (2013.01)

(58) Field of Classification Search
None
See application file for complete search history.

(56) References Cited

U.S. PATENT DOCUMENTS

| | | |
|---|---|---|
| 7,488,721 B2 | 2/2009 | Mahuran et al. |
| 7,858,655 B2 | 12/2010 | Rohnert et al. |
| 2003/0171391 A1 | 9/2003 | Gaida et al. |
| 2004/0219207 A1 * | 11/2004 | Rohnert ............ A61K 45/06 424/465 |
| 2004/0242700 A1 | 12/2004 | Kido |
| 2006/0008862 A1 | 1/2006 | Mahuran et al. |
| 2006/0276393 A1 | 12/2006 | Milburn et al. |
| 2006/0276416 A1 | 12/2006 | Sinclair et al. |
| 2007/0149466 A1 | 6/2007 | Milburn et al. |
| 2007/0172856 A1 | 7/2007 | Hogaboam et al. |
| 2007/0244184 A1 | 10/2007 | Pinto et al. |

FOREIGN PATENT DOCUMENTS

WO 0002553 A 1/2000

OTHER PUBLICATIONS

Gibbs, et al., "Ambroxol Inhibits the Release of Histamine, Leukotrienes and Cytokines from Human Leukocytes and Mast Cells", Journal of Inflammatory Research, 48: 86-93 (1999).
Grinzaid, et al., "Cessation of Enzyme Replacement Therapy in Gaucher Disease", Genetics in Medicine, 4: 427-433 (2002) (Abstract only).
Heath, et al., "The Inhibition of Lysosomal Phospholipase A from Rabbit Lung by Ambroxol and Its Consequences for Pulmonary Surfactant", Lung, 163: 337-344 (1985).
Hruska, et al., Gaucher Disease: Mutation and Polymorphism Spectrum in the Glucocerebrosidase Gene (GBA), Human Mutation, 29(5): 567-583 (2008).
Mahuran, et al., "Identification of Ambroxol as a Potential Enzyme Enhancement-Agent for Gaucher Disease", Molecular Genetics and Metabolism, Lysosomal Disease Network-World Symposium 2008 Preliminary Program, Nov. 26, 2007 (http://www.lysosomaldiseasenetwork.org/ldn_ world_symposium_2008 _ pro- gram. shtml).
Radin, et al., "Treatment of Gaucher Disease with an Enzyme Inhibitor", Glycoconjugate Journal, 13: 153-157 (1996).
The Merck Manual of Diagnosis and Therapy—Eighteenth Edition, 2006, p. 2469-2470.
Tropak, et al., "Effects of Novel Beta-Glucocerebrosidase Enhancers and Pharmacological Chaperones on Protein Stability/Dynamics Probed by Hydrogen-Deuterium Exchange Mass Spectrometry", Molecular Genetics and Metabolism, 93(2): S40, (2008).
Wilke, et al., "Ambroxol Increases the Choline but Not Fatty Acid Incorporation into Lung Phospholipids in Experimental Lung Disorders", Respiration, 52: 129-136 (1987).
www.ntsad.org (accessed online Jun. 1, 2010).
www.wrongdiagnosis.com (accessed online Jun. 1, 2010).
Kornhaber, et al., Isofagomine Induced stabilization of glucocerebrosidase, Chembiochem, 9(16): 2643-2649 (2008).

(Continued)

*Primary Examiner* — Craig Ricci
(74) *Attorney, Agent, or Firm* — Michele M. Wales; InHouse Patent Counsel, LLC

(57) ABSTRACT

Therapeutic compositions and methods for treatment of late-onset Gaucher disease are described herein. The compositions comprise compounds having activity as pharmacological chaperones for mutant forms of the beta-glucocerebrosidase. Methods of treatment involve providing therapeutically effective amounts of such compositions to subjects in need thereof.

31 Claims, 6 Drawing Sheets

(56) References Cited

OTHER PUBLICATIONS

Maegawa, et al., "Identification and Characterization of Ambroxol as an Enzyme Enhancement Agent for Gaucher Disease", Journal of Biological Chemistry, (284)35: 23502-23516 (2009).

Lu, et al., Histone Deacetylase Inhibitors Prevent the Degradation and Restore the Activity of Glucocerebrosidase in Gaucher Disease, PNAS, 108(52): 21200-21205 (2011).

Coker-Alpan, et al., Divergent Phenotypes in Gaucher Disease Implicate the Role of Modifiers, Journal of Medical genetics, 42(6): e37 (2005).

* cited by examiner

METHODS OF TREATING PARKINSON'S DISEASE

CROSS REFERENCE TO RELATED APPLICATIONS

This Application is a continuing application of and claims priority to U.S. Ser. No. 14/255,324 which was filed on Apr. 17, 2014, now U.S. Pat. No. 9,233,083, which is a continuation of U.S. patent application Ser. No. 13/676,506, filed Nov. 14, 2012, now U.S. Pat. No. 8,951,994, which is a divisional of U.S. patent application Ser. No. 13/248,434, filed Sep. 29, 2011, now U.S. Pat. No. 8,404,668, which is a divisional of U.S. patent application Ser. No. 12/229,445, filed Aug. 22, 2008, now U.S. Pat. No. 8,124,597, the entire disclosures of which are incorporated herein by reference, which claims the filing date benefit of the following U.S. Provisional Applications, the entire disclosures of which are incorporated herein by reference: No. 60/972,968, filed Sep. 17, 2007; No. 61/065,550, filed Feb. 12, 2008, and No. 61/065,684, filed Feb. 13, 2008.

FIELD OF THE INVENTION

The invention relates to the use of small molecule compounds to treat Gaucher Disease.

BACKGROUND OF THE INVENTION

Lysosomal storage disorders (LSD's) are a group of diseases resulting from the abnormal metabolism of various substrates, including glycosphingolipids, glycogen, mucopolysaccharides and glycoproteins. The metabolism of exo- and endogenous high molecular weight compounds normally occurs in the lysosomes, and the process is normally regulated in a stepwise process by degradation enzymes. For example, the enzymes beta-glucocerebrosidase and alpha-galactosidase are involved in the catabolism of glycosphingolipids.

A deficient activity in even one catabolic enzyme may impair the process, resulting in an accumulation of particular substrates. As part of lysosomal processing, the enzyme beta-glucocerebrosidase (referred to interchangeably herein as "GCase" or "Gcc") cleaves the terminal glucose residue from glucosylceramide. A deficiency in GCase—in the form of one or more amino acid mutations—results in the LSD reduced, little, or no glucosylceramide cleavage activity, depending upon the mutated amino acid or amino acids. The severity of this disorder is correlated with relative levels of residual enzyme activity and the resulting extent of accumulation of the substrate.

Currently, Gaucher patients are treated using an expensive enzyme replacement therapy at a cost of about $300,000 USD per year per patient, or by using non-specific substrate reduction therapy. With these treatments, the enzyme deficiency itself is not treated, but rather, the accumulation of substrate is treated by reducing the synthetic levels of all gangliosides.

What is needed is an efficient and less-expensive way to treat individuals having Gaucher disease. The present invention addresses and meets this need.

Bromhexine, and its metabolite ambroxol, are expectoration improvers and mucolytic agents used in the treatment of respiratory disorders associated with viscid or excessive mucus. They work to decrease mucus viscosity by altering its structure. Neither bromhexine or ambroxol have been known to have any activity relevant to the treatment of lysosomal storage disorders.

SUMMARY OF THE INVENTION

The invention relates to a method of treating an individual suffering from Gaucher disease, comprising administering to the individual an effective amount of ambroxol, or a derivative thereof. The invention also relates to ambroxol, or a derivative thereof, as a medicament for treatment of Gaucher disease. The invention also relates to a composition for the treatment of Gaucher disease comprising a therapeutically effective amount of ambroxol, or a derivative thereof, together with a pharmaceutically acceptable excipient. The invention also comprises a method of dosing ambroxol, or derivative thereof, to achieve optimal pharmacological chaperoning and enzyme enhancement.

In some embodiments, the ambroxol derivative comprises a cyclohexane ring, an amine group, and/or at least two bromine groups. In some embodiments, the derivative comprises a compound listed in Table 2. In some embodiments, the derivate is an enantiomer, analog, ester, amide, prodrug, or metabolite of ambroxol, or a salt of ambroxol, particularly a pharmaceutically acceptable salt. In some embodiments, the ambroxol derivative is bromhexine or a salt of bromhexine. In some embodiments, the salt of ambroxol or bromhexine is a hydrochloride.

In an embodiment of the treatment method of the invention, the individual also suffers from Parkinson's disease.

The invention also relates to a method of treating an individual suffering from Gaucher disease, comprising administering to the individual an effective amount of a compound listed in Table 1. The invention also relates to a compound listed in Table 1, as a medicament for treatment of Gaucher disease. The invention also relates to a composition for treatment of Gaucher disease comprising a therapeutically effective amount of a compound listed in Table 1, together with a pharmaceutically acceptable excipient. The administered compound may optionally comprise a salt of a compound of Table 1, particularly a pharmaceutically acceptable salt. In an embodiment of the treatment method, the individual also suffers from Parkinson's disease.

In any of the aforesaid methods and compositions, the therapeutic compound may comprise a beta-glucocerebrosidase inhibitor that demonstrates beta-glucocerebrosidase pharmacological chaperone activity.

In another embodiment, the invention includes a method of inducing a stable conformation of a glucocerebrosidase, the method comprising contacting the glucocerebrosidase with ambroxol, or a derivative thereof. The invention also relates to a composition for inducing a stable conformation of a glucocerebrosidase comprising ambroxol, or a derivative thereof. In some embodiments of the composition and method for inducing a stable conformation of a glucocerebrosidase, the ambroxol derivative comprises a cyclohexane ring, an amine group, and/or at least two bromine groups. In some embodiments, the ambroxol derivative comprises a compound listed in Table 2. In some embodiments, the derivate is an enantiomer, analog, ester, amide, prodrug, or metabolite of ambroxol, or a salt of ambroxol, particularly a pharmaceutically acceptable salt. In some embodiments, the ambroxol derivative is bromhexine or a salt of bromhexine. In some embodiments, the salt of ambroxol or bromhexine is a hydrochloride.

In further embodiments, the invention includes (i) a method of inducing a stable conformation of a glucocerebrosidase, the method comprising contacting the glucocerebrosidase with a compound of Table 1, and (ii) a composition for inducing a stable conformation of a glucocerebrosidase comprising a compound of Table 1. The compound may optionally comprise a salt of a compound of Table 1, particularly a pharmaceutically acceptable salt.

In one embodiment of the method for inducing a stable conformation of a glucocerebrosidase, the glucocerebrosidase is contacted with ambroxol or derivative thereof, or with a compound of Table 1, in vitro. In another embodiment, the contact of the glucocerebrosidase occurs in vivo.

In some embodiments of the method for inducing a stable conformation of a glucocerebrosidase, the glucocerebrosidase is selected from the group consisting of a wild type glucocerebrosidase, a mutant glucocerebrosidase, and an engineered glucocerebrosidase.

BRIEF DESCRIPTION OF THE DRAWINGS

Embodiments of the present invention will now be described, by way of example only, with reference to the attached Figures.

FIG. 4a shows the GCase activity determined by a fluorometric assay and FIG. 4b shows the GCase protein levels as determined by densitometry.

FIG. 5a shows the GCase activity determined by a fluorometric assay and FIG. 5b shows the GCase protein levels as determined by densitometry.

(FIG. 6A, staining with anti-GCase in the presence of ABX; FIG. 6B, staining with anti-Lamp-1 in the presence of ABX; FIG. 6C, merger of FIGS. 6A and 6B; FIG. 6D, staining with anti-GCase in the presence of IFG; FIG. 6E, staining with anti-Lamp-1 in the presence of IFG; FIG. 6F, merger of FIGS. 6D and 6E; FIG. 6G, staining with anti-GCase in the absence of drug; FIG. 6H, staining with anti-Lamp-1 in the absence of drug; FIG. 6I, merger of FIGS. 6G and 6H.)

ABBREVIATIONS AND SHORT FORMS

Figure 1:
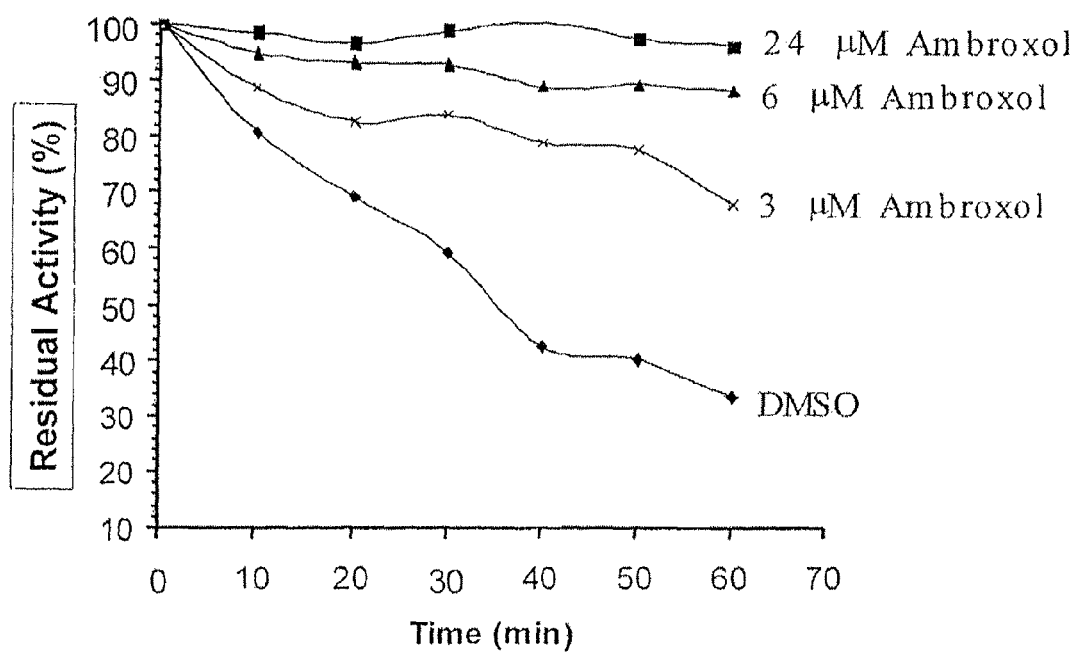
FIG. 1 shows a heat denaturation curve of GCase in the presence of ambroxol. These data illustrate that increasing concentrations of ambroxol attenuate thermal denaturation of GCase.

The following abbreviations and short forms are used in this specification:

"ABX" refers to ambroxol.
"GCase" refers to beta-glucocerebrosidase.
"PC" refers to a pharmacological chaperone.
"IFG" refers to isofagomine.

DETAILED DESCRIPTION

I. Definitions

As used in the specification and the appended claims, the singular forms "a," "an" and "the" include plural referents unless the context clearly dictates otherwise.

The expressions "treat" and "treatment" mean cause, or the act of causing, a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

The expression "effective amount", when used to describe therapy to an individual, refers to the amount of a compound that results in a therapeutically useful effect.

As used herein, "individual" (as in the subject of the treatment) means mammals, particularly non-human primates, e.g. apes and monkeys, and most particularly humans.

The term "isolated compound" means a compound substantially free of contaminants or cell components with which the compound naturally occur, or the reagents used in synthesis or the byproducts of synthesis. "Isolated" and "substantially free of contaminants" does not mean that the preparation is technically pure (homogeneous), but it is sufficiently pure to provide the compound in a form in which it can be used therapeutically.

A "derivative" compound, as the term is used herein, refers to a second compound that is derived from a first compound, such as a brominated version of a non-brominated parent compound. For example, bromhexine is a derivative of ambroxol.

II. Compounds of the Invention

Current therapies for Gaucher therapies are either expensive, or treat the symptoms, but not the underlying cause of the disease. In contrast, the present invention describes compounds for use as "pharmacological chaperones", and presents an opportunity to treat patients at a reduced costs and with increased specificity.

Ambroxol, derivatives of ambroxol (e.g., bromhexine), and salts thereof are pharmacological chaperones (PC's), and as set forth in detail elsewhere herein, enhance the amounts of mutant enzyme that can be transported to and/or accumulated in the lysosome. Representative derivatives of ambroxol are set forth in Table 2, below. These compounds may be used as therapeutics for lysosomal storage disorders that are characterized by a mutant enzyme having reduced residual catalytic activity in the lysosome due to retention of the mutant enzyme in the endoplasmic reticulum. Other compounds useful as therapeutics for lysosomal storage disorders that are characterized by a mutant enzyme having reduced residual catalytic activity in the lysosome due to retention of the mutant enzyme in the endoplasmic reticulum include derivatives of ambroxol, as well as compounds that are GCase inhibitors having GCase pharmacological chaperone activity, set forth in Table 1, below.

Ambroxol, also known by its chemical name trans-4-(2-amino-3,5-dibromobenzylamino) cyclohexanol, has the structure:

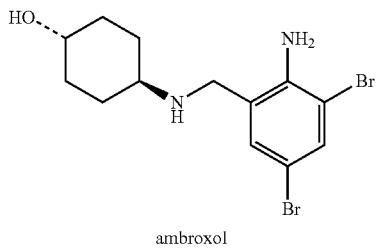 [SMILES: Nc1c(Br)cc(Br)cc1CN[C@H]1CC[C@H](O)CC1]

ambroxol

An aspect of the invention also includes a medicament, for the treatment of Gaucher disease, comprising a pharmaceutically acceptable salt of ambroxol. In one embodiment, the salt is a hydrochloride salt.

Bromhexine, also known by its chemical name 2-amino-3,5-dibromo-N-cyclohexyl-N-methylbenzenemethanamine, has the structure:

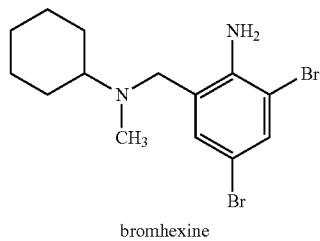 [SMILES: CN(Cc1cc(Br)cc(Br)c1N)C1CCCCC1]

bromhexine

An aspect of the invention also includes a medicament, for the treatment of Gaucher disease, comprising a pharmaceutically acceptable salt of bromhexine. In one embodiment, the salt is a hydrochloride salt.

Another aspect of the invention includes a pharmaceutically acceptable salt of a derivative of ambroxol.

Yet another aspect of the invention includes a medicament, for the treatment of Gaucher disease, comprising a compound having inhibitory activity against GCase. Table 1 lists compounds identified as GCase inhibitors, which are believed to act as pharmacological chaperones.

TABLE 1

Beta-glucocerebrosidase inhibitors in GenPlus NINDS collection

| Compound Name | Structure |
| --- | --- |
| CHLORPROMAZINE | 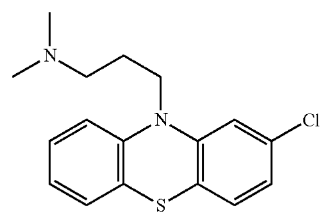 [SMILES: CN(C)CCCN1c2ccccc2Sc2ccc(Cl)cc21] |
| DIENESTROL | 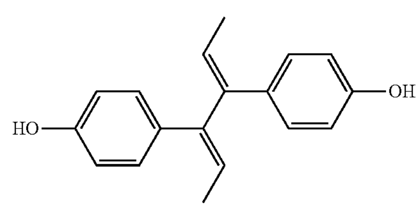 [SMILES: C/C=C(/C(=C/C)c1ccc(O)cc1)c1ccc(O)cc1] |
| DIFLUNISAL | 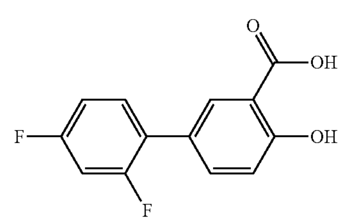 [SMILES: O=C(O)c1cc(-c2ccc(F)cc2F)ccc1O] |

TABLE 1-continued
Beta-glucocerebrosidase inhibitors in GenPlus NINDS collection
| Compound Name | Structure |
|---|---|
| FLUMETHAZONE PIVALATE | 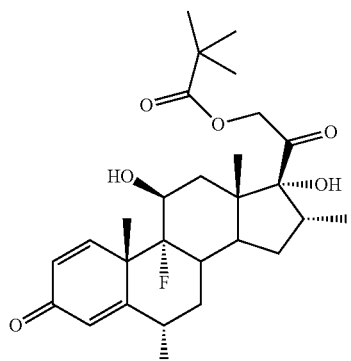 |
| GENTIAN VIOLET | 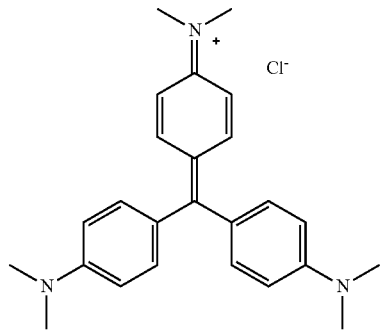 |
| GUANABENZ ACETATE | 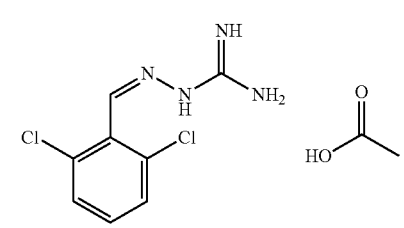 |
| MAPROTILINE HYDROCHLORIDE | 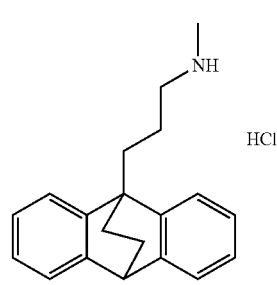 [SMILES: CNCCCC12CCC(c3ccccc31)c1ccccc12 ; Cl] |
| MECLIZINE HYDROCHLORIDE | 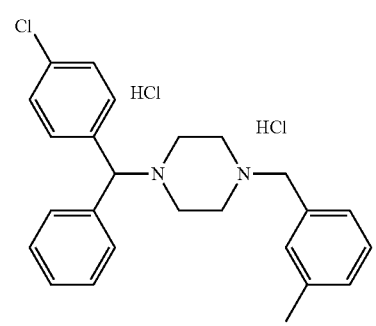 [SMILES: Cc1cccc(CN2CCN(C(c3ccccc3)c3ccc(Cl)cc3)CC2)c1 ; Cl ; Cl] |

TABLE 1-continued
Beta-glucocerebrosidase inhibitors in GenPlus NINDS collection
| Compound Name | Structure |
|---|---|
| GLUCONOLACTONE | 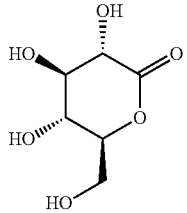 [SMILES: O=C1O[C@@H](CO)[C@H](O)[C@@H](O)[C@@H]1O] |
| HALCINONIDE | 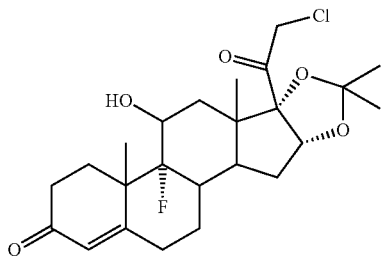 |
| PARAROSANILINE PAMOATE | 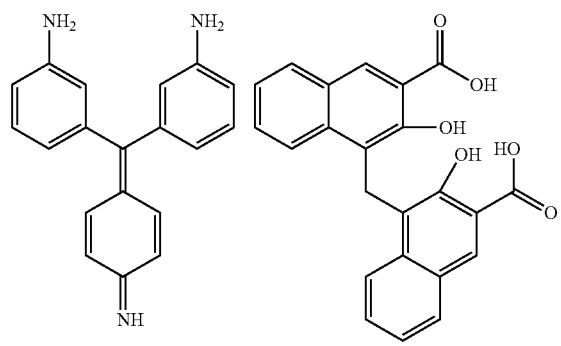 |
| ENOXACIN | 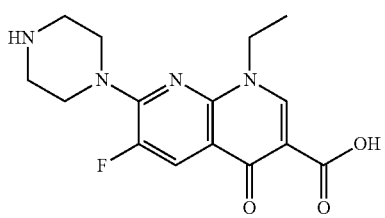 [SMILES: CCn1cc(C(=O)O)c(=O)c2cc(F)c(N3CCNCC3)nc21] |
| CINNARAZINE | 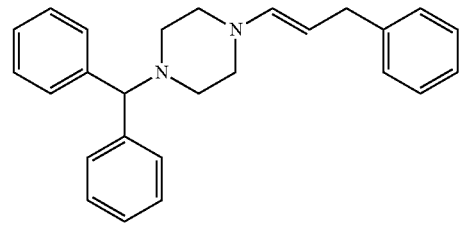 [SMILES: C(=C\N1CCN(C(c2ccccc2)c2ccccc2)CC1)/Cc1ccccc1] |
| PERHEXILINE MALEATE | 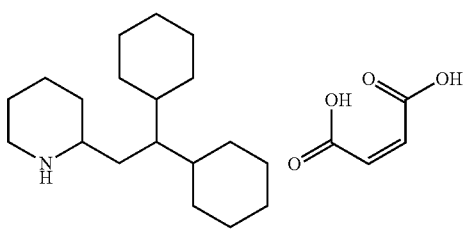 |

TABLE 1-continued

Beta-glucocerebrosidase inhibitors in GenPlus NINDS collection

| Compound Name | Structure |
| --- | --- |
| AMBROXOL HYDROCHLORIDE | 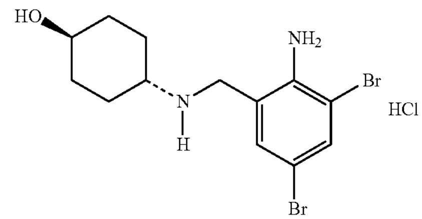 [SMILES: Nc1c(Br)cc(Br)cc1CN[C@H]1CC[C@H](O)CC1 ; Cl] |
| ECONAZOLE NITRATE | 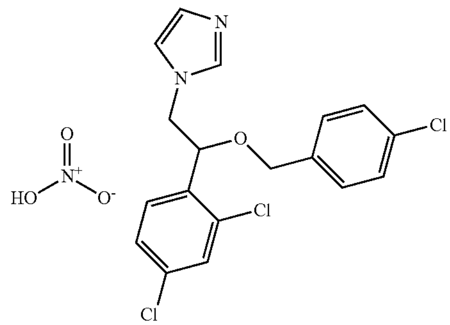 |
| SULCONAZOLE NITRATE | 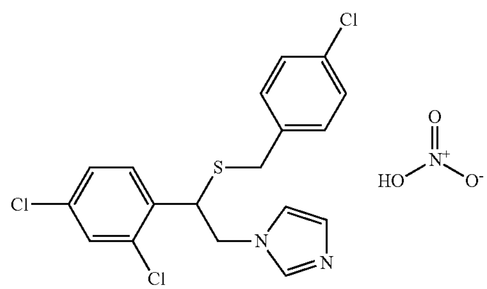 |
| CLOMIPRAMINE HYDROCHLORIDE | 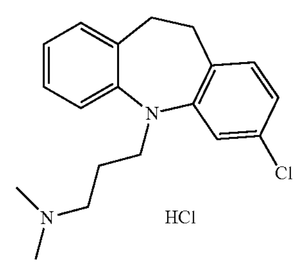 [SMILES: CN(C)CCCN1c2ccccc2CCc2ccc(Cl)cc21 ; Cl] |
| ASTEMIZOLE | 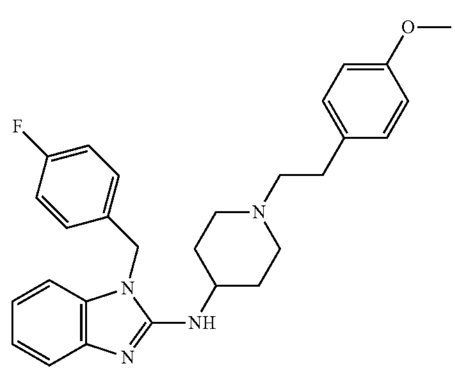 [SMILES: COc1ccc(CCN2CCC(Nc3nc4ccccc4n3Cc3ccc(F)cc3)CC2)cc1] |

TABLE 1-continued
Beta-glucocerebrosidase inhibitors in GenPlus NINDS collection
| Compound Name | Structure |
|---|---|
| HOMIDIUM BROMIDE | 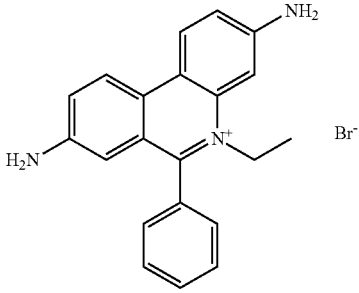 [SMILES: CC[n+]1c(-c2ccccc2)c2cc(N)ccc2c2ccc(N)cc21 ; [Br-]] |
| SELAMECTIN | 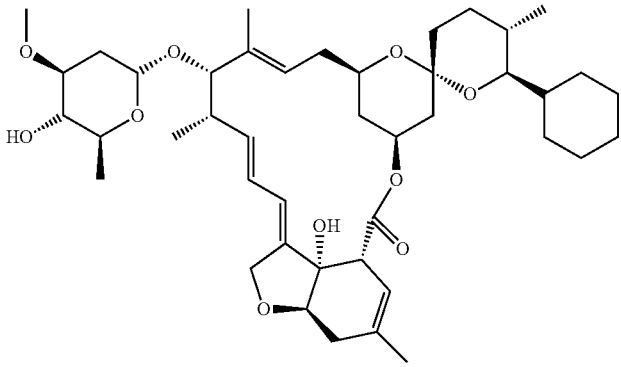 |
| HYDROXYTACRINE MALEATE | 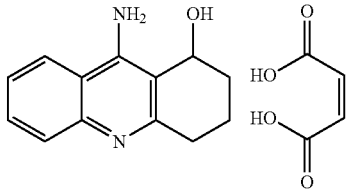 |
| THIORIDAZINE HYDROCHLORIDE | 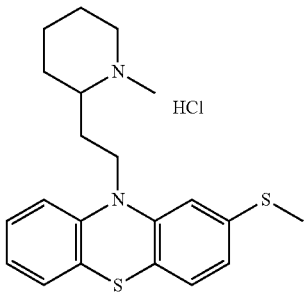 [SMILES: CSc1ccc2c(c1)N(CCC1CCCCN1C)c1ccccc1S2 ; Cl] |
| PYRVINIUM PAMOATE | 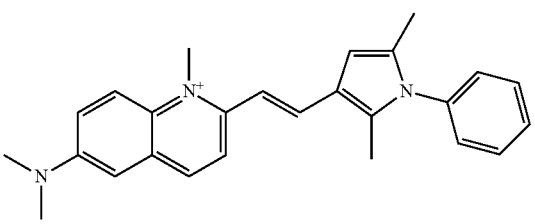 [SMILES: Cc1cc(/C=C/c2ccc3cc(N(C)C)ccc3[n+]2C)c(C)n1-c1ccccc1] |

TABLE 1-continued
Beta-glucocerebrosidase inhibitors in GenPlus NINDS collection
| Compound Name | Structure |
|---|---|
| | 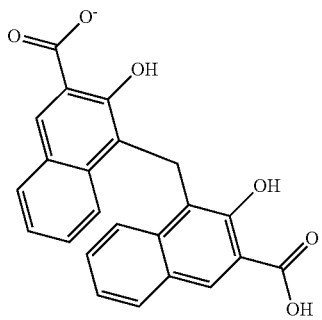 [SMILES: O=C([O-])c1cc2ccccc2c(Cc2c(O)c(C(=O)O)cc3ccccc23)c1O] |
| PHENOLPHTHALEIN | 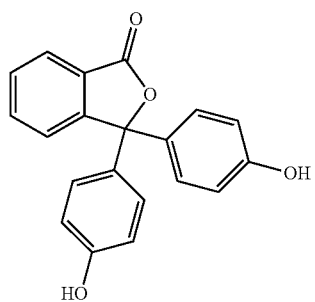 [SMILES: O=C1OC(c2ccc(O)cc2)(c2ccc(O)cc2)c2ccccc21] |
| NOSCAPINE HYDROCHLORIDE | 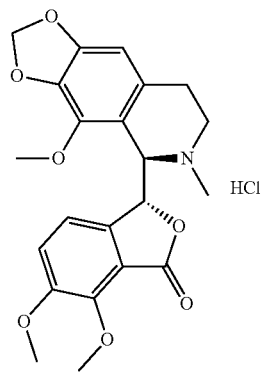 [SMILES: COc1ccc2c(c1OC)C(=O)O[C@H]2[C@H]1c2c(cc3c(c2OC)OCO3)CCN1C ; Cl] |
| PHENAZOPYRIDINE HYDROCHLORIDE | 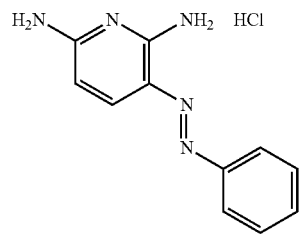 [SMILES: Nc1ccc(/N=N/c2ccccc2)c(N)n1 ; Cl] |

TABLE 1-continued
Beta-glucocerebrosidase inhibitors in GenPlus NINDS collection
| Compound Name | Structure |
|---|---|
| RESERPINE | 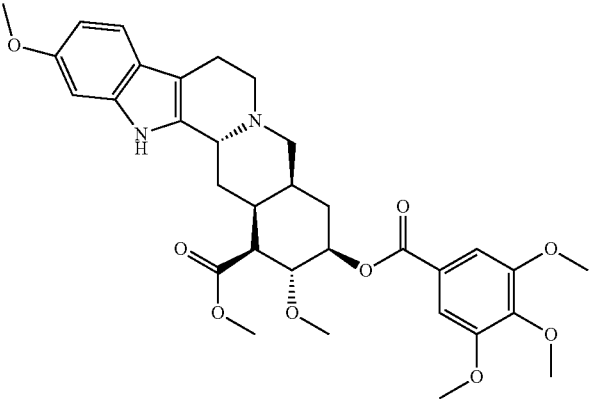 |
| TAMOXIFEN CITRATE | 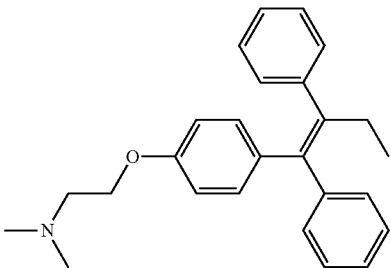 [SMILES: CC/C(=C(\c1ccccc1)c1ccc(OCCN(C)C)cc1)c1ccccc1] |
| PERPHENAZINE | 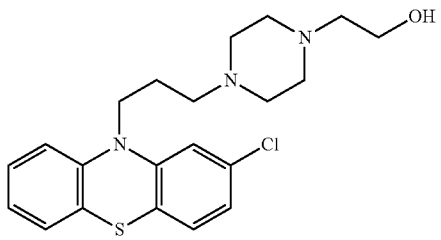 [SMILES: OCCN1CCN(CCCN2c3ccccc3Sc3ccc(Cl)cc32)CC1] |
| LANSOPRAZOLE | 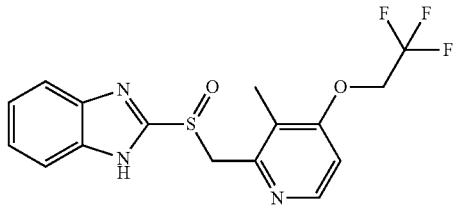 [SMILES: Cc1c(OCC(F)(F)F)ccnc1CS(=O)c1nc2ccccc2[nH]1] |

TABLE 1-continued
Beta-glucocerebrosidase inhibitors in GenPlus NINDS collection
| Compound Name | Structure |
| --- | --- |
| AMOXEPINE | 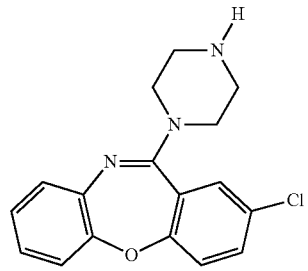 [SMILES: Clc1ccc2c(c1)C(N1CCNCC1)=Nc1ccccc1O2] |
| PHENOXYBENZAMINE HYDROCHLORIDE | 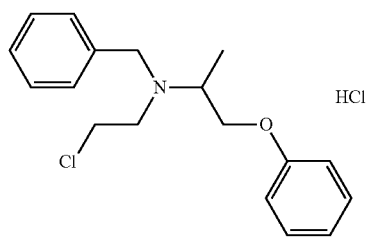 [SMILES: CC(COc1ccccc1)N(CCCl)Cc1ccccc1 ; Cl] |
| CLOPERASTINE HYDROCHLORIDE | 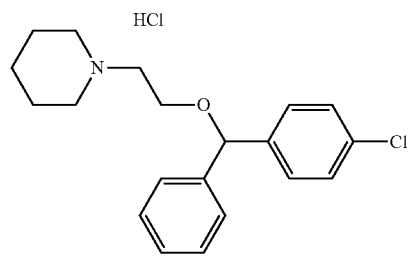 [SMILES: Cl ; Clc1ccc(C(OCCN2CCCCC2)c2ccccc2)cc1] |
| THYROXINE | 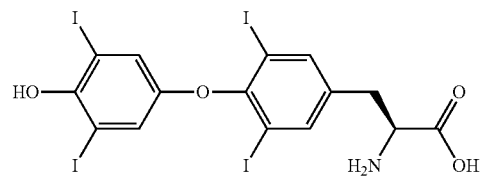 [SMILES: N[C@@H](Cc1cc(I)c(Oc2cc(I)c(O)c(I)c2)c(I)c1)C(=O)O] |
| NARINGENIN | 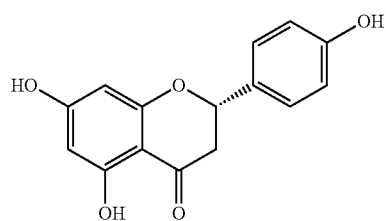 [SMILES: O=C1C[C@@H](c2ccc(O)cc2)Oc2cc(O)cc(O)c21] |

TABLE 1-continued
Beta-glucocerebrosidase inhibitors in GenPlus NINDS collection
| Compound Name | Structure |
|---|---|
| PIMOZIDE | 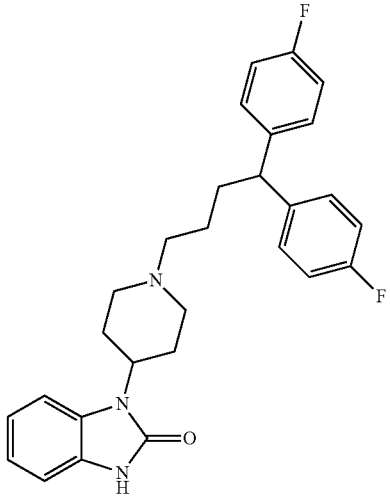 [SMILES: O=c1[nH]c2ccccc2n1C1CCN(CCCC(c2ccc(F)cc2)c2ccc(F)cc2)CC1] |
| NICARDIPINE HYDROCHLORIDE | 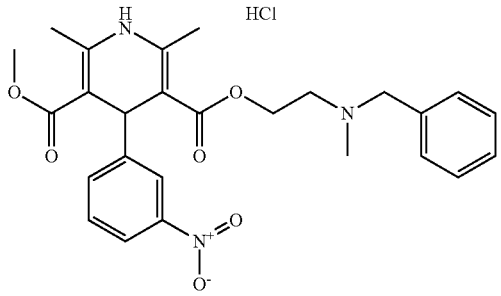 [SMILES: Cl ; COC(=O)C1=C(C)NC(C)=C(C(=O)OCCN(C)Cc2ccccc2)C1c1cccc([N+](=O)[O-])c1] |
| N,N-HEXAMETHYLENEAMILORIDE | 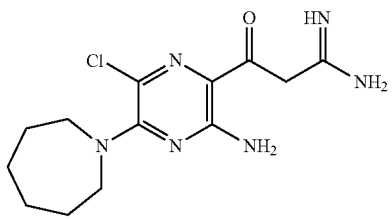 [SMILES: N=C(N)CC(=O)c1nc(Cl)c(N2CCCCCC2)nc1N] |
| 2,3-DIHYDROXY-6,7-DICHLOROQUINOXALINE | 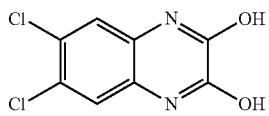 [SMILES: Oc1nc2cc(Cl)c(Cl)cc2nc1O] |
| MIGLITOL | 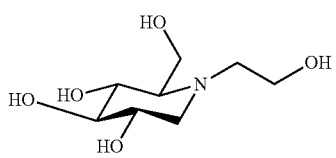 |

TABLE 1-continued

Beta-glucocerebrosidase inhibitors in GenPlus NINDS collection

| Compound Name | Structure |
|---|---|
| RITANSERIN | *(structure shown)* |
| DIMERCAPTOPROPANOL | *(structure shown)* |
| HYCANTHONE | *(structure shown)* |
| APIGENIN | *(structure shown)* |

Table 2, below, illustrates structures of various Ambroxol derivatives and variants, together with the $IC_{50}$ values (in micromolar, results obtained from an assay using 0.3 mM MUbGlc as the substrate.

As can be seen in Table 2, compounds such as tribromophenyl propanoate are less effective inhibitors of GCase, whereas compounds comprising a secondary hydrophobic group in the form of a more flexible cyclohexane ring are good inhibitors. Bromhexine shows a two fold reduction in inhibitory activity compared with ambroxol. Dibromophenyl derivatives bearing a alkyl amine with a flexible hydrophobic ring moiety are thus candidates for possessing inhibitory activity against GCase. Therefore, another aspect of the invention includes a derivative of ambroxol, wherein the derivative comprises an alkyl amine with a flexible hydrophobic ring moiety.

TABLE 2

Ambroxol derivatives demonstrating activity against human beta-glucocerebrosidase

| Compound ($IC_{50}$, micromolar) | Structure |
|---|---|
| Ambroxol (27) | *(structure shown)* |

TABLE 2-continued

Ambroxol derivatives demonstrating activity against human beta-glucocerebrosidase

| Compound (IC$_{50}$, micromolar) | Structure |
| --- | --- |
| Tribromophenyl Propanoate (>1000) | 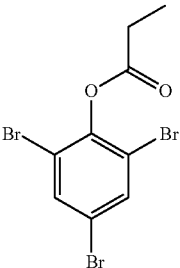 |
| Dibromophenyl Benzamide (>1000) | 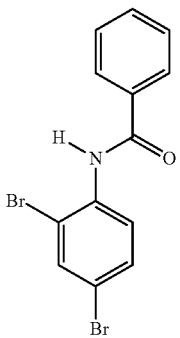 [SMILES: O=C(Nc1ccc(Br)cc1Br)c1ccccc1] |
| Bromehexine (60) | 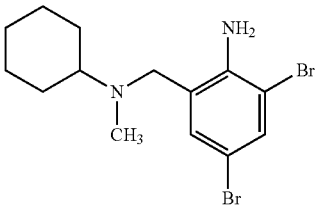 [SMILES: CN(Cc1cc(Br)cc(Br)c1N)C1CCCCC1] |
| Dibromoaniline (NI-1000) | 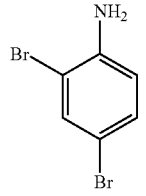 |
| Tribromoaniline (NI-1000) | 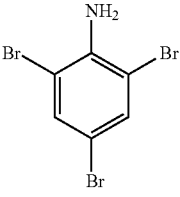 | a. Preparation of Compounds of the Invention

The compounds of the invention are known and may be prepared by methods known to the person skilled in the art of organic synthesis. For example, U.S. Patent Application publication number US2004/0242700, incorporated herein by reference in its entirety, provides a synthetic protocol for the preparation of ambroxol.

b. Salts of Compounds of the Invention

For compounds that typically contain acidic or basic groups (such as amine or carboxyl groups) such groups will not necessarily be in the free base form. When referring to compounds of the invention, the reference is intended to include salt forms of the compound. Within the scope of the invention, therefore, are salts of the active agent, especially salts of ambroxol and bromhexine. The preferred salts are pharmaceutically-acceptable salts. Also within the scope of the invention are salts of derivatives of ambroxol.

The term "salts" embraces addition salts of free acids or free bases. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of therapeutic compounds.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, oxalic, malonic and galacturonic acid. Examples of pharmaceutically unacceptable acid addition salts include, for example, perchlorates and tetrafluoroborates. All of these acid addition salts may be prepared from ambroxol or bromhexine by reacting, for example, the appropriate acid with the compound.

Suitable pharmaceutically acceptable base addition salts of ambroxol include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these base addition salts may be prepared from ambroxol by reacting, for example, the appropriate base with the compound.

c. Pharmaceutical Compositions

In an aspect, the invention includes a composition comprising a therapeutically effective amount of ambroxol, derivatives of ambroxol, such as bromhexine, or a pharmaceutically acceptable salt thereof, in conjunction with a pharmaceutically acceptable excipient for treatment of an individual suffering from Gaucher disease. In another aspect, the invention includes a composition comprising a therapeutically effective amount of ambroxol or a derivative thereof, inclusive of pharmaceutically acceptable salts thereof, in conjunction with a pharmaceutically acceptable excipient for treatment of Gaucher disease in an individual suffering from both Gaucher disease and Parkinson's disease. In yet another aspect, the invention includes a composition comprising a therapeutically effective amount of a derivative of ambroxol, including, but not limited to an enantiomer, analog, ester, amide, prodrug, or metabolite of ambroxol, or a pharmaceutically acceptable salt thereof, in conjunction with a pharmaceutically acceptable excipient for treatment of an individual suffering from Gaucher disease. Reports of Parkinson's disease associated with type I Gaucher's disease have been documented, suggesting a genetic link between the two diseases (Intern Med. (2006) 45(20):1165-1167).

In another aspect, the invention includes a composition comprising a therapeutically effective amount of a GCase inhibitor from Table 2 that demonstrates GCase PC activity, or a pharmaceutically acceptable salt thereof, in conjunction with a pharmaceutically acceptable excipient for treatment of Gaucher disease in an individual suffering from Gaucher disease. In yet another aspect, the invention includes a composition comprising a therapeutically effective amount of a GCase inhibitor from Table 2 that demonstrates GCase PC activity, or a pharmaceutically acceptable salt thereof in conjunction with a pharmaceutically acceptable excipient for treatment of Gaucher disease in an individual suffering from both Gaucher disease and Parkinson's disease.

The active agent (e.g., ambroxol, derivatives of ambroxol, compounds of Table 1, or pharmaceutically acceptable salts thereof) may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions. For examples of the preparation of oral, topical, suppository and parenteral formulations of ambroxol, also useful for administration of bromhexine, or other ambroxol derivatives, or for a GCase inhibitor that demonstrates GCase PC activity, see Examples 1-8 of WO2005/007146, or its equivalent US2005/00148747, incorporated herein by reference.

In another embodiment, ambroxol, a derivative of ambroxol, or a GCase inhibitor that demonstrates GCase PC activity, is used in the preparation of a medicament for the treatment of Gaucher disease.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 50 to about 1000 mg, more typically, about 250 to about 500 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted- and programmed-release formulations. Sustained or controlled release can be obtained by using, for example, poly(D,L-lactic-co-glycolic acid).

III. Activity of the Compounds of the Invention

A functional compound which is able to induce a stable molecular conformation of an enzyme, such as beta-glucocerebrosidase (GCase), can serve as a "pharmacological chaperone" (PC) for the enzyme by stabilizing the enzyme in a proper conformation for transport to the lysosome. In one aspect, the compound induces a stable molecular conformation of a wild type enzyme for transport to the lysosome. In an aspect, the compound induces a stable molecular conformation of a mutant enzyme for transport to the lysosome. In another aspect, the compound induces a stable molecular conformation of an engineered enzyme for transport to the lysosome.

A "wild type enzyme," as used herein, refers to an enzyme that has the amino acid sequence of the enzyme as encoded by the gene for the enzyme. An "engineered" enzyme, as the term is used herein, refers to an enzyme that has been modified through one or more techniques such as, but not limited to, recombinant protein production, site-directed mutagenesis, chemical modification, in vitro glycosylation, and in vivo glycosylation. A "mutant" enzyme, as used herein, refers to an enzyme that has an amino acid sequence that differs from the wild type sequence by one or more amino acids. A mutant enzyme may have the same number of amino acids as the wild type enzyme, or the mutant enzyme may have at least one more or at least one fewer amino acid residue than the wild type enzyme. A mutant enzyme may occur naturally or may be engineered, as described herein.

In an embodiment of the invention, an effective amount of compound is used to induce the stable conformation. Some inhibitors of the enzyme are known to occupy the catalytic center of the enzyme, resulting in stabilization of its conformation in vitro. The inhibitors may bind to the native enzyme, the wild type enzyme, or to recombinantly-produced enzyme obtained from any source, including, but not limited to bacterial cells, insect cells, plant cells and mammalian cells. Other compounds may bind close to, but not on, the active site. Yet, other compounds may bind at a distance from the active site while stabilizing the enzyme as allosteric pharmacological chaperones. All such compounds may also serve as PC's to enforce the proper folding of the enzyme in vivo, and thus rescue the mutant enzyme from degradation by the endoplasmic reticulum quality control system.

In an aspect of the invention, ambroxol, a derivative of ambroxol, or a GCase inhibitor that demonstrates GCase PC activity, such as a compound of Table 1, or pharmaceutically acceptable salt thereof, has the property of functioning as a chaperone, also referred to herein as a PC, for GCase. As used herein, "pharmacological chaperone" means that a compound of the invention has the ability to facilitate and/or enhance the transport of a biological molecule across a membrane or into a subcellular compartment. In particular, a pharmacological chaperone of the invention is a compound that has the ability to facilitate or enhance the transport of GCase into the lysosome. In another aspect, the aforementioned compounds demonstrate inhibitory activity with respect to GCase.

A PC can stabilize its target enzyme (e.g., ambroxol stabilization of GCase or mutant GCase) into a stable conformation and thus allow the enzyme to successfully avoid the endoplasmic reticulum-associated degradation system. The ability of the compounds to bind to GCase and facilitate the transport of GCase into the lysosome is assayed using a GCase assay as set forth in detail in the Example below. In an embodiment of the invention, a compound binding and/or GCase chaperone assay is conducted by assaying GCase activity in isolated fibroblast cells.

While not wishing to be bound by any particular theory or mechanism of action, ambroxol and derivatives thereof function as specific molecular guides for a mutant GCase and enhance GCase activity in the lysosome. It has been found that at least ambroxol binds to mutant GCase with a low affinity at the pH of the endoplasmic reticulum, thereby promoting proper folding of GCase. The enhancement of proper folding enhances the chaperoning of GCase to the lysosome by ambroxol. In the lysosome, ambroxol dissociates from GCase due to the very low affinity of ambroxol for GCase at lysosomal pH. Furthermore, because of the high concentration of accumulated glucocerebrosides in the lysosome, the glucocerebrosides, which are natural substrates of GCase, shift the binding equilibrium to displace ambroxol from GCase.

IV. Methods of Treatment Using Compounds of the Invention

Ambroxol, a derivative of ambroxol, or a GCase inhibitor of Table 1 that demonstrates GCase PC activity, or pharmaceutically acceptable salts thereof, are used for the treatment of Gaucher disease, which can benefit from increased GCase activity in the lysosome. The increased transport of GCase into the lysosome, and thereby, the increased concentration of GCase in the lysosome, will increase the GCase activity in the lysosome. Even mutant forms of GCase, such as the mutant GCase forms characteristic of Gaucher disease, which have low levels of GCase activity when compared with wild type (i.e., non-mutated) GCase, can increase GCase activity in the lysosome when transported to the lysosome.

Thus, in one aspect, a compound as described above is administered to treat Gaucher disease. The method comprises administering an effective amount of the compound, or a pharmaceutical composition comprising such a compound, to an individual in need of such treatment.

Gaucher disease is a condition in which a patient suffers from an accumulation of glycosphingolipids. This disease arises because of a deficiency in the GCase enzyme responsible for the catabolism of the glycosphingolipids. An increase in the GCase activity in the lysosomes of patients afflicted with Gaucher disease can treat the disease by enhancing the catabolism of the accumulating glycosphingolipids. Therefore, an individual who is in need of treatment with a compound according to the invention can be an individual who is suffering from one or more symptoms of Gaucher disease.

In an aspect, the patient treated for Gaucher's disease is characterized by a mutation in the gene encoding GCase, wherein the resulting enzyme mutation is selected from the group consisting of V15L, G46E, K79N, R119Q, P122S, R131L, K157Q, N188S, Y212H, F213I, F216V, F216Y, F251L, R257E, P289L, A309V, H311R, W312C, Y323I, G325R, C342G, R353G, R359X (termination), S364T, N370S, L371V, G377S, V394L, V398F, P401L, D409H, D409V, P415R, L444P, R463C, G478S, R496H. In another aspect, the patient is characterized by more than one mutation in the gene encoding GCase, selected from the group consisting of (L444P, A456P, V460V), (D140H, E326K), and (H255Q, D409H). In yet another aspect, the patient is characterized by an insertion, deletion, truncation, or frameshift mutation, or combination thereof, in the gene encoding the GCase, selected from the group consisting of:
 84GG (guanine insertion),
 splice site mutation in intron 2 (IVS2DS+1G-A), resulting in the skipping of exon 2,
 a 1-bp deletion (1023delC in the genomic sequence) in the GCase gene,
 a 55-bp deletion (nucleotides 5879-5933 in genomic DNA) in the GCase gene,
 a homozygous 259C-T transition (1763 in the genomic DNA)
 a homozygous 1-bp deletion in the GCase gene, resulting in a frameshift and premature truncation of the protein in exon 6, and
 G-to-A substitution at the first position in the splice site of intron 10 of the GCase gene, resulting in the insertion of the first 11 basepairs of IVS10 and deletion of the first 11 basepairs of exon 11.

In one aspect, the patient treated for Gaucher's disease is characterized by a mutation in the gene encoding GCase, wherein the resulting enzyme mutation is selected from the group consisting of N370S and L444P.

In another aspect, a compound of the invention is used to treat Gaucher disease in a patient having both Gaucher disease and Parkinson's Disease. The method comprises administering an effective amount of a compound as described above, or a pharmaceutical composition comprising the compound, as described herein, to an individual in need of such treatment.

In one embodiment, a method of the invention includes treating an individual suffering from Gaucher disease comprising administering to the individual an effective amount of ambroxol or derivative thereof. In another embodiment, a method of the invention includes treating an individual suffering from both Gaucher disease and Parkinson's disease comprising administering to the individual an effective amount of ambroxol or derivative thereof. In yet another embodiment, a method of the invention includes treating an individual suffering from Gaucher disease comprising administering to the individual an effective amount of a derivative of ambroxol or derivative thereof, or a GCase inhibitor that demonstrates GCase PC activity. In another embodiment, a method of the invention includes treating an individual suffering from both Gaucher disease and Parkinson's disease comprising administering to the individual an effective amount of ambroxol or derivative thereof, or a GCase inhibitor that demonstrates GCase PC activity. In each of the aforesaid embodiments, the administered compound may comprise a salt, particularly a pharmaceutically acceptable salt. In some embodiments, the salt is a hydrochloride salt.

The amount of the therapeutic compound of the invention that will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

V. Administration of Compounds of the Invention

In a preferred embodiment, the compounds of the invention are administered orally to a patient. However, the compounds may be administered by any route, including by rectal, pulmonary, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration.

Typically it is contemplated that treatment would be given in a dose sufficient to achieve concentrations where the chaperone binds to and stabilizes GCase and in a dosing interval long enough to effect low concentrations of the chaperone and dissociation from the enzyme. These optimal pharmacokinetic properties depend on the bioavailability and the elimination half-life of the chaperone. The dosing interval may be once a week, twice a week, every-other-day, once per day, typically once, twice, three times or four times per day with the doses given at equal intervals throughout the day and night in order to maintain a constant presence of the drug in order to induce sufficient transport of GCase into the lysosome. However, the skilled artisan will be aware that a treatment schedule can be optimized for any given patient, and that administration of compound may occur less frequently than once per day.

One or more compounds of the invention may be administered simultaneously, by the same or different routes, or at different times during treatment. The compounds of the invention may also be prescribed to be taken in combination with other drugs used to treat Gaucher disease and/or Parkinson's disease. When used in such combinations compounds of the invention and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

The specific dose of a compound according to the invention to obtain therapeutic benefit for treatment of Gaucher disease will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Example below, there can be employed conventional clinical, chemical, cellular, histochemical, biochemical, molecular biology, microbiology and recombinant DNA techniques which are known to those of skill in the art. Such techniques are explained fully in the literature.

Without further description, it is believed that one of ordinary skill in the art can, using the preceding description and the following illustrative example, make and utilize the compounds of the present invention and practice the claimed methods. The following working example therefore, specifically points out the preferred embodiments of the present invention, and is not to be construed as limiting in any way the remainder of the disclosure.

Example

Chaperoning of Wild Type Beta-Glucocerebrosidase and Gaucher Disease Mutant Beta-Glucocerebrosidases by Compounds of the Invention A. Assay Conditions for GCase Activity and Function Studies.

Experiments set forth herein and related to the activity and function of GCase in the presence and absence of compounds of the invention were conducted using imiglucerase (CEREZYME, Genzyme) as the GCase. Cellular materials were obtained from fibroblast lysates expressing wild-type GCase and separately from fibroblast lysates derived from Gaucher disease patient cell lines carrying genotypes that encode either the N370S/N370S or F213I/L444P substitutions in GCase.

Quantitative determinations of enzymatic activity were performed by way of fluorometric assays utilizing the artificial substrate 4-methylumbelliferyl 2-acetamido-2-deoxy-beta-D-glucopyranoside (MUGlc). Reactions were performed at room temperature for 15-30 minutes, as indicated, using equal aliquots of enzyme (25 µL 20 mM Citrate Phosphate pH 5.5, 0.4% Taurodeoxycholate (TC)) and substrate (25 µL 20 mM Citrate Phosphate pH 5.5, MUGlc 1.6 mM). The amount of MU-fluorophore released in each assay was monitored fluorometrically using a spectrophotofluorometer following the addition of a 4-fold (200 µl) excess of 0.1M MAP, pH 10.5. The observed activity is either expressed in relative fluorescence units (FUs), as a percentage of the activity observed in untreated GCase controls (% residual activity), or as the fold-increase as compared to lysates from untreated cells (relative increase in activity).

Confluent cultures of patient fibroblasts were grown in 24-well plates. Following a five day treatment of the fibroblasts with either DMSO or test compound, the cells were washed twice with phosphate buffered saline, then lysed on ice for 30 minutes using 20 mM citrate-phosphate buffer, pH 5.5, containing 0.4% TC. GCase activity was analyzed in a 25 µl aliquot of the cell lysate using the same protocol described above for the purified enzyme.

B. Thermal Stability of GCase in the Presence of Ambroxol.

FIG. 1 shows a heat denaturation curve of GCase in the presence of ambroxol at concentrations of 3 µM, 6 µM and 24 µM. Ambroxol was shown to attenuate thermal denaturation of wild type (WT) GCase, increasing the half life at 50° C., more than three-fold at a concentration of 20 µM. The data illustrate that increasing concentrations of ambroxol attenuate thermal denaturation of GCase, evidencing ambroxol binding to GCase.

GCase was also incubated in the presence of increasing concentrations of ambroxol or DMSO (control, compound solvent) at 50° C. for varying periods of time. Similar to samples maintained at 4° C., the fraction of GCase activity remaining after incubation at 50° C. increased in samples containing increasing concentrations of ambroxol as compared to samples containing only DMSO. The increase in GCase activity in the presence of the highest concentration of ambroxol was more than three-fold.

C. Kinetic Analysis of GCase Activity in the Presence of Ambroxol and Other GCase Inhibitors.

Figure 2:
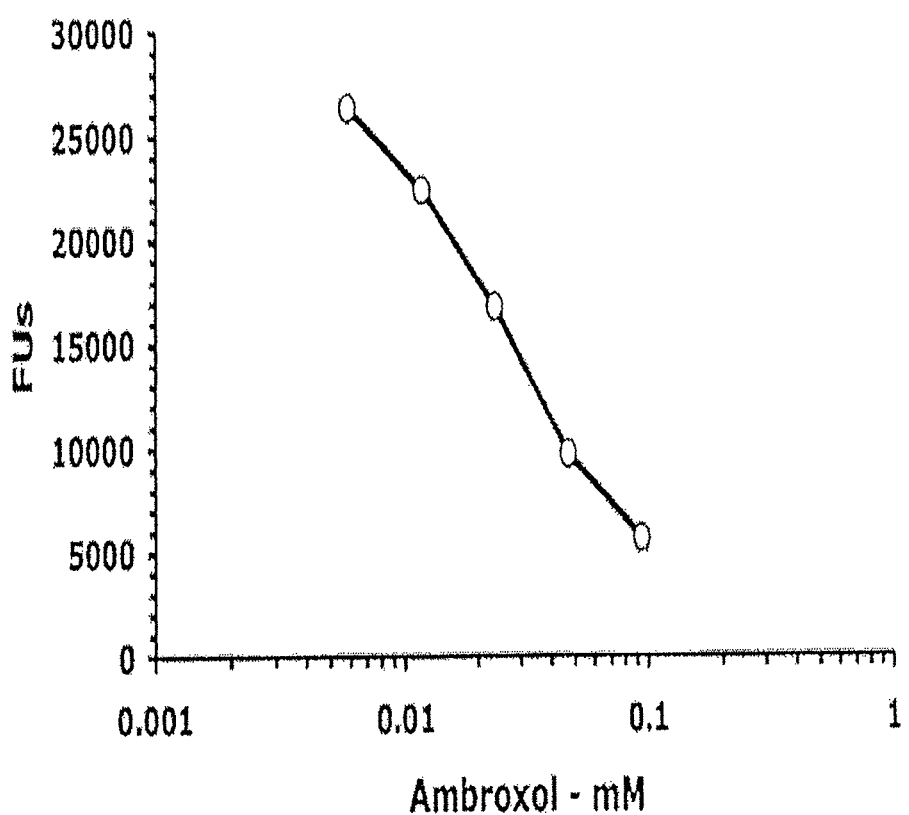
FIG. 2 shows the activity of GCase (CEREZYME) in the presence of increasing concentrations of ambroxol. An IC50 of 27 µM was determined in this assay.

FIG. 2 shows the activity of GCase in the presence of increasing concentration of ambroxol. Kinetic analysis showed ambroxol to be a competitive inhibitor of GCase with a $K_i$ of 10 µM. The $IC_{50}$ for ambroxol as an inhibitor of GCase was determined to be 27 μM (FIG. 2). The $IC_{50}$ for bromhexine was determined to be 60 μM.

An additional experiment was conducted to compare the activity of ambroxol with the activity of the known GCase inhibitor, isofagomine. Ambroxol and isofagomine both attenuated thermal denaturation of wild type (WT) GCase, increasing the half life of GCase more than three-fold at a concentration of 20 μM, at 50° C. Significantly, ambroxol binds to misfolded GCase with lower affinity than that of isofagomine at the pH of the endoplasmic reticulum, where ambroxol promotes proper GCase folding, and thus, enhances GCase traffic to the lysosome. In the lysosome, ambroxol dissociates from GCase due to the very low affinity of ambroxol for GCase at lysosomal pH. Furthermore, the accumulated glucocerobrosides (the natural substrates of GCase) in the lysosome also serve to displace ambroxol. While not wishing to be bound by any particular theory, ambroxol may be less likely to be trapped in the lysosome than isofagomine, and therefore, the risk that long-term treatment with ambroxol will cause ambroxol to accumulate in the lysosome at a concentration sufficient to become a GCase inhibitor and paradoxically cause Gaucher disease is lower than for isofagomine.

Figure 3:
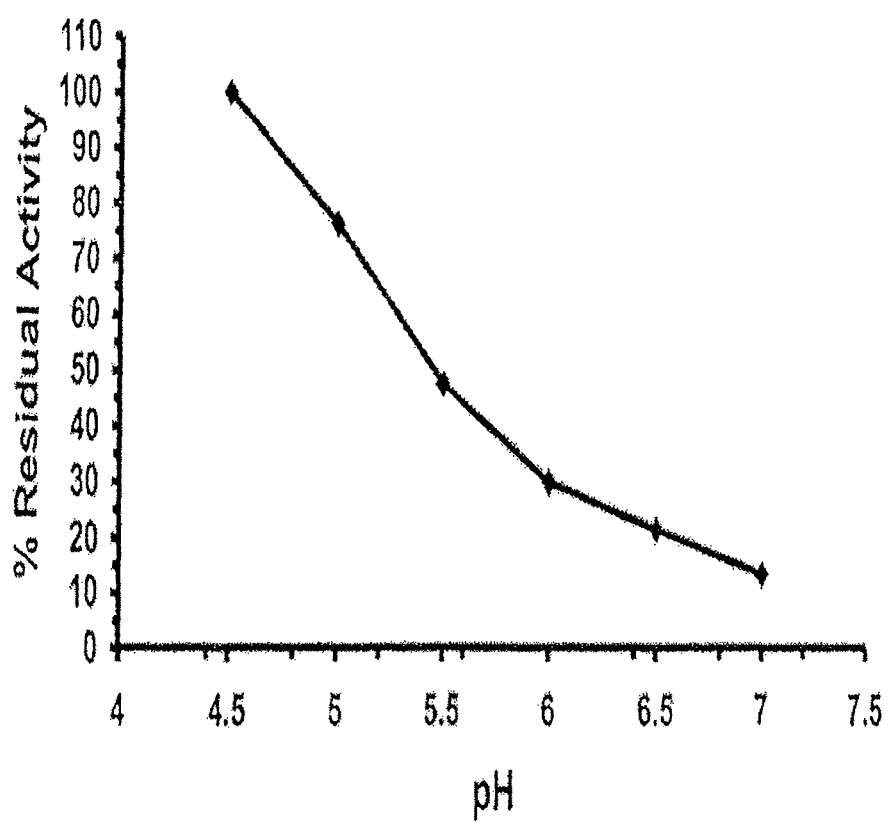
FIG. 3 shows the activity of GCase (CEREZYME) at several different pH values, in the presence of ambroxol. The data illustrates that 25 µM ambroxol only marginally inhibited GCase under acidic conditions.

The activity of GCase was also assayed at several different pH values, including 4.5, 5.0, 5.5, 6.0, 6.5 and 7.0. As a point of reference, the pH of the lysosome is acidic (pH<5.5) and the pH of the endoplasmic reticulum is near neutral. As shown in FIG. 3, ambroxol only marginally inhibited GCase under acidic conditions.

This finding supports the role of ambroxol and derivatives thereof as pharmacological chaperones (PC's). In order for a PC to stabilize its target protein (e.g., ambroxol stabilization of GCase or mutant GCase) and thus allow the enzyme to successfully avoid the endoplasmic reticulum-associated degradation system, a PC should possess an appropriate level of binding-affinity at neutral pH. Following enzyme-ligand complex formation at neutral pH and the subsequent successful trafficking of the enzyme to its appropriate organelle (in the present case, the acidic lysosome), a drop in affinity would be advantageous to facilitate the displacement of the inhibitory PC by the native substrate of the enzyme or the mutant enzyme.

The data set forth herein demonstrates that the affinity of ambroxol for GCase would be low to negligible following incorporation into the low-pH lysosome, and that the affinity of GCase for ambroxol would be maximal in the pH-neutral ER, the location where affinity is most desirable. Thus, the data set forth herein demonstrate that ambroxol is an excellent therapeutic pharmacological chaperone for GCase.

D. Ambroxol as a Pharmacological Chaperone of GCase.

Figure 4A:
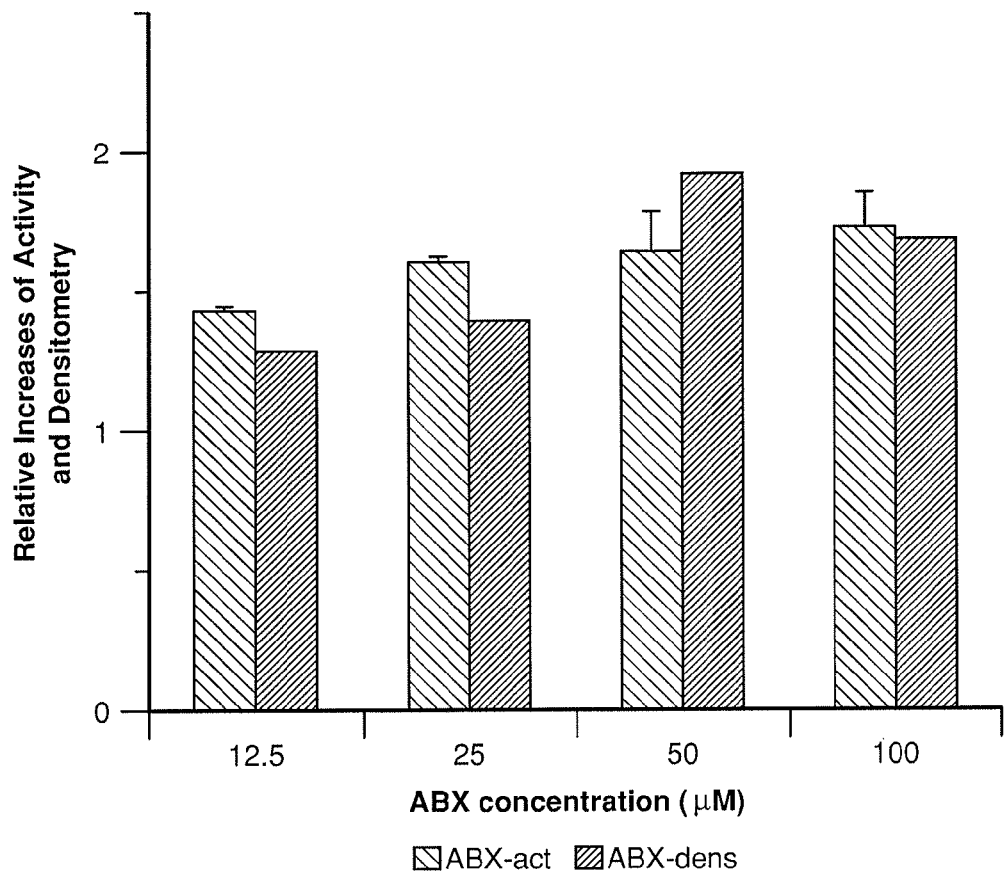
FIGS. 4a and 4b show that ambroxol (abbreviated as ABX) enhanced both the activity and concentration of wild-type GCase in fibroblasts that were pre-treated with ambroxol.
Figure 4B:
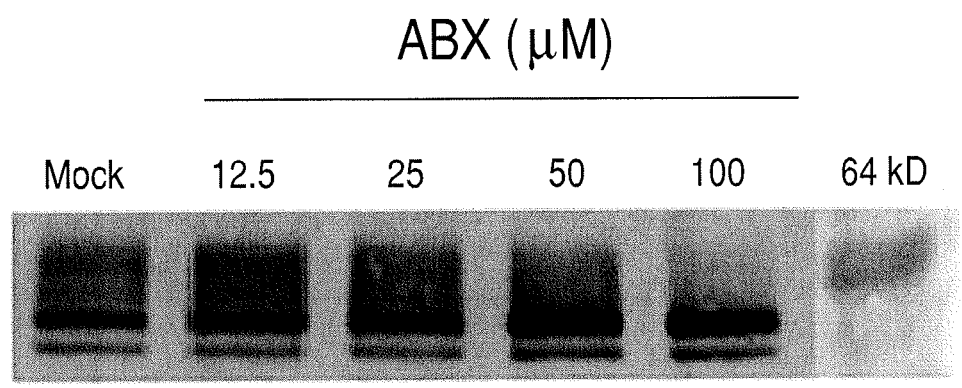

Fibroblasts expressing wild-type GCase were treated with ambroxol for 5 days prior to measuring GCase activity levels within the cells. Ambroxol (abbreviated "ABX" in FIG. 4a and FIG. 4b) was found to enhance both the GCase activity and the levels of wild-type GCase by more than one and half times that of non-treated cells. FIG. 4a shows the GCase activity determined by a fluorometric assay. FIG. 4b shows the GCase protein levels as determined by densitometry.

Figure 5A:
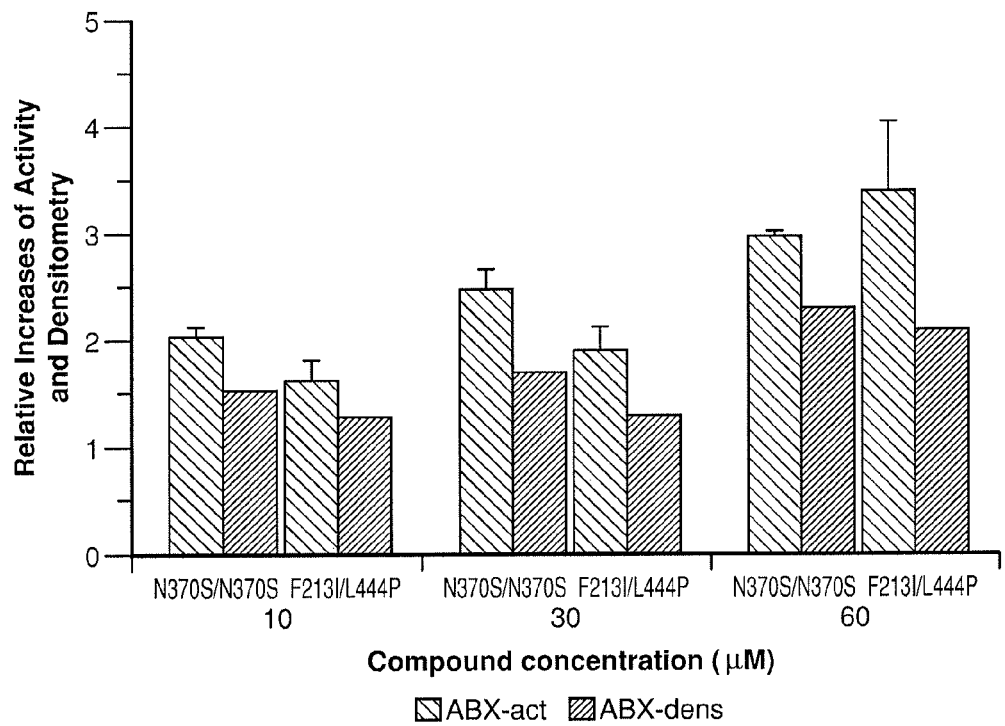
FIGS. 5a and 5b show that ambroxol (abbreviated as ABX) enhanced both the activity and protein levels of mutant GCase in Gaucher disease fibroblast cell lines harboring either the N370S/N370S or F213I/L444P sets of missense mutations commonly associated with the most frequently occurring type I form of Gaucher disease.
Figure 5B:
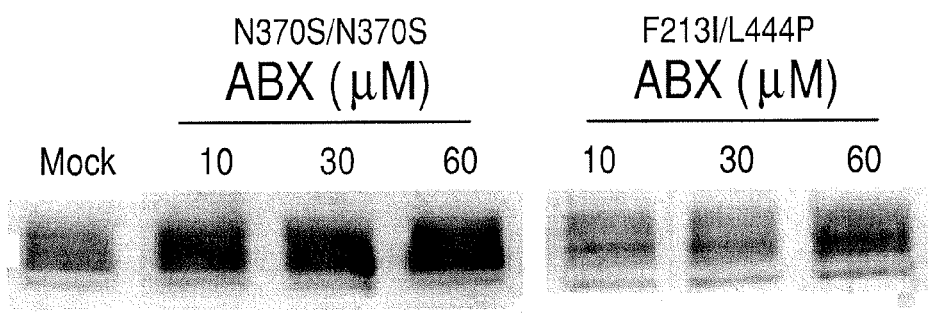

Even greater increases of GCase activity and enzyme levels were observed in Gaucher disease patient-derived fibroblast cell lines harboring the Gaucher disease associated genotypes N370S/N370S and F213I/L444P. FIGS. 5a and 5b show that ambroxol (abbreviated as ABX) enhanced both the activity and protein levels of mutant GCase in Gaucher disease fibroblast cell lines harboring either the N370S/N370S or F213I/L444P sets of missense mutations. These mutations are commonly associated with the most frequently occurring type I form of Gaucher disease. FIG. 5a shows the GCase activity determined by a fluorometric assay. FIG. 5b shows the GCase protein levels as determined by densitometry.

GCase activity and GCase concentration in the presence of 60 μM ambroxol were approximately 3 and 2.5 times the activity and concentration of non-treated Gaucher disease patient fibroblasts, respectively. Type I Gaucher disease patients have residual enzyme levels that are approximately 10-15% of normal. The data set forth herein suggests that, similar to other lysosomal storage disorders, it appears that only a relatively small increase in GCase activity is necessary to treat the clinical progression of the disease.

Figures 6A, 6B, 6C:
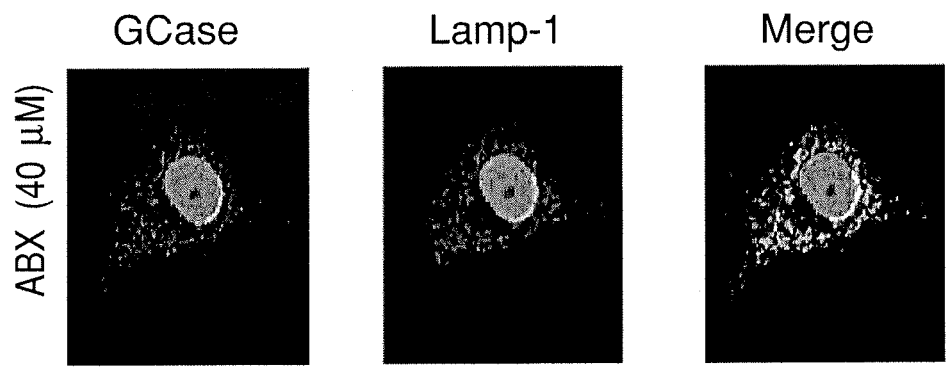
FIGS. 6A-6I show the rescue of mutant GCase trafficking by ambroxol (abbreviated as ABX) compared to isofagomine (abbreviated as IFG) and untreated controls ("Mock"). Immunohistochemical fluorescence labeling of GD fibroblast cell lines harboring the N370S/N370S missense mutation were performed with rabbit polyclonal anti-GCase and mouse anti-Lamp-1 (lysosomal membrane associated protein). Cell nuclear staining was performed with 4'-6'-diamidino-2-phenylindole. Colocalization of GCase and Lamp-1 occurs at the lysosome in the presence of ambroxol ("ABX"), and to a lesser degree in the presence of isofagomine ("IFG").
Figures 6D, 6E, 6F:
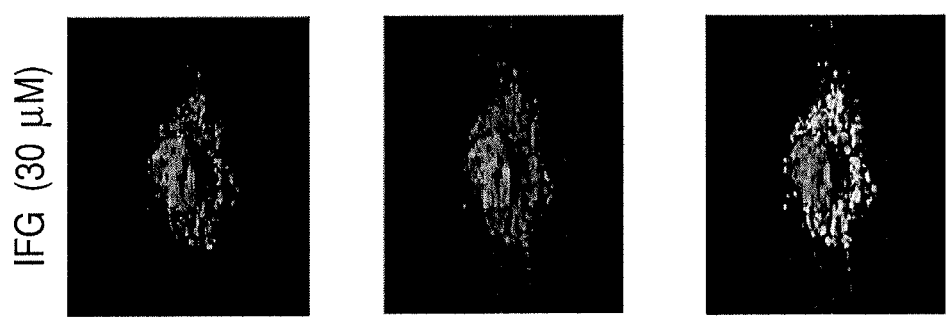
Figures 6G, 6H, 6I:
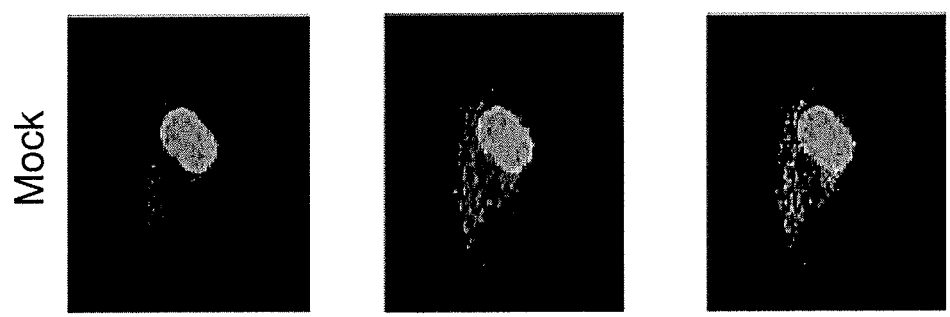

Immunohistochemical fluorescence labeling of Gaucher disease fibroblast cell lines harboring the N370S/N370S missense mutation was performed with rabbit polyclonal anti-GCase and mouse anti-Lamp-1 (lysosomal membrane associated protein). Cell nuclear staining was performed with 4'-6'-diamidino-2-phenylindole. Colocalization of GCase and Lamp-1 in the presence of ambroxol is indicative of rescued trafficking and lysosomal delivery of GCase. Restored activity and trafficking of mutant GCase are the ultimate goals of a pharmacological chaperone-based therapeutic strategy. FIGS. 6A-6I shows the rescue of mutant GCase trafficking by ambroxol (abbreviated as ABX). Colocalization of GCase and Lamp-1 occurs at the lysosome in the presence of ambroxol ("ABX"; FIG. 6C), and to a lesser degree in the presence of isofagomine ("IFG"; FIG. 6F).

In summary, compounds set forth herein, including ambroxol and derivatives thereof, attenuate thermal denaturation of GCase and act as pharmacological chaperones for GCase into the lysosome. Accordingly, they are useful for the treatment of patients suffering from Gaucher disease and also of Gaucher disease patients who may also be suffering from Parkinson's disease.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing the symptoms of Parkinson's Disease in a patient comprising administering to the patient ambroxol, ambroxol hydrochloride, or bromhexine, or a pharmaceutically acceptable salt thereof at a dose of 250-500 mg administered once, twice, three or four times a day.

2. The method of claim 1, comprising administering ambroxol or a pharmaceutically acceptable salt thereof.

3. The method of claim 2, wherein said patient is also administered another drug for the treatment of Gaucher's Disease.

4. The method of claim 2, wherein said patient has Gaucher's Disease.

5. The method of claim 2, wherein the patient is also administered a recombinant glucocerebrosidase.

6. The method of claim 5, wherein the recombinant glucocerebrosidase is imiglucerase.

7. The method of claim 2, wherein said patient has a mutation in the gene encoding a beta glucocerebrosidase.

8. The method of claim 7, wherein the mutation in the gene encoding a beta glucocerebrosidase is selected from:
   a. A point mutation comprising V15L, G46E, K79N, R119Q, P122S, R131L, K157Q, N188S, Y212H, F213I, F216V, F216Y, F251L, R257E, P289L, A309V, H311R, W312C, Y323I, G325R, C342G, R353G, R359X (termination), S364T, N370S, L371V, G377S, V394L, V398F, P401L, D409H, D409V, P415R, L444P, R463C, G478S, or R496H;
b. Point mutations at L444P, A456P, and V460V;
c. Point mutations at D140H and E326K;
d. Point mutations at H255Q and D409H;
e. Guanine insertion at 84GG;
f. Splice site mutation in intron 2 (IVS2DS+1G-A), resulting in the skipping of exon 2;
g. A 1-bp deletion (1023delC in the genomic sequence) in the GCase gene,
h. A 55-bp deletion (nucleotides 5879-5933 in genomic DNA) in the GCase gene;
i. A homozygous 259C-T transition (1763 in the genomic DNA)
j. A homozygous 1-bp deletion in the GCase gene, resulting in a frameshift and premature truncation of the protein in exon 6; and
k. A G-to-A substitution at the first position in the splice site of intron 10 of the GCase gene, resulting in the insertion of the first 11 base pairs of IVS10 and deletion of the first 11 base pairs of exon 11.

9. The method of claim 8, wherein the mutation in the gene encoding a beta-glucocerebrosidase comprises N370S.

10. The method of claim 8, wherein the mutation in the gene encoding a beta-glucocerebrosidase comprises L444P.

11. The method of claim 8, wherein the mutation in the gene encoding a beta-glucocerebrosidase comprises E326K.

12. The method of claim 1, comprising administering ambroxol hydrochloride.

13. The method of claim 12, wherein said patient is also administered another drug for the treatment of Gaucher's Disease.

14. The method of claim 12, wherein said patient has Gaucher's Disease.

15. The method of claim 12, wherein the patient is also administered a recombinant glucocerebrosidase.

16. The method of claim 15, wherein the recombinant glucocerebrosidase is imiglucerase.

17. The method of claim 12, wherein said patient has a mutation in the gene encoding a beta glucocerebrosidase.

18. The method of claim 17, wherein the mutation in the gene encoding a beta glucocerebrosidase is selected from:
a. A point mutation comprising V15L, G46E, K79N, R119Q, P122S, R131L, K157Q, N188S, Y212H, F213I, F216V, F216Y, F251L, R257E, P289L, A309V, H311R, W312C, Y323I, G325R, C342G, R353G, R359X (termination), S364T, N370S, L371V, G377S, V394L, V398F, P401L, D409H, D409V, P415R, L444P, R463C, G478S, or R496H;
b. Point mutations at L444P, A456P, and V460V;
c. Point mutations at D140H and E326K;
d. Point mutations at H255Q and D409H;
e. Guanine insertion at 84GG;
f. Splice site mutation in intron 2 (IVS2DS+1G-A), resulting in the skipping of exon 2;
g. A 1-bp deletion (1023delC in the genomic sequence) in the GCase gene,
h. A 55-bp deletion (nucleotides 5879-5933 in genomic DNA) in the GCase gene;
i. A homozygous 259C-T transition (1763 in the genomic DNA)
j. A homozygous 1-bp deletion in the GCase gene, resulting in a frameshift and premature truncation of the protein in exon 6; and
k. A G-to-A substitution at the first position in the splice site of intron 10 of the GCase gene, resulting in the insertion of the first 11 base pairs of IVS10 and deletion of the first 11 base pairs of exon 11.

19. The method of claim 18, wherein the mutation in the gene encoding a beta-glucocerebrosidase comprises N370S.

20. The method of claim 18, wherein the mutation in the gene encoding a beta-glucocerebrosidase comprises L444P.

21. The method of claim 18, wherein the mutation in the gene encoding a beta-glucocerebrosidase comprises E326K.

22. The method of claim 1, comprising administering bromhexine or a pharmaceutically acceptable salt thereof.

23. The method of claim 22, wherein said patient is also administered another drug for the treatment of Gaucher's Disease.

24. The method of claim 22, wherein said patient has Gaucher's Disease.

25. The method of claim 22, wherein the patient is also administered a recombinant glucocerebrosidase.

26. The method of claim 25, wherein the recombinant glucocerebrosidase is imiglucerase.

27. The method of claim 22, wherein said patient has a mutation in the gene encoding a beta glucocerebrosidase.

28. The method of claim 27, wherein the mutation in the gene encoding a beta glucocerebrosidase is selected from:
l. A point mutation comprising V15L, G46E, K79N, R119Q, P122S, R131L, K157Q, N188S, Y212H, F213I, F216V, F216Y, F251L, R257E, P289L, A309V, H311R, W312C, Y323I, G325R, C342G, R353G, R359X (termination), S364T, N370S, L371V, G377S, V394L, V398F, P401L, D409H, D409V, P415R, L444P, R463C, G478S, or R496H;
m. Point mutations at L444P, A456P, and V460V;
n. Point mutations at D140H and E326K;
o. Point mutations at H255Q and D409H;
p. Guanine insertion at 84GG;
q. Splice site mutation in intron 2 (IVS2DS+1G-A), resulting in the skipping of exon 2;
r. A 1-bp deletion (1023delC in the genomic sequence) in the GCase gene,
s. A 55-bp deletion (nucleotides 5879-5933 in genomic DNA) in the GCase gene;
t. A homozygous 259C-T transition (1763 in the genomic DNA)
u. A homozygous 1-bp deletion in the GCase gene, resulting in a frameshift and premature truncation of the protein in exon 6; and
v. A G-to-A substitution at the first position in the splice site of intron 10 of the GCase gene, resulting in the insertion of the first 11 base pairs of IVS10 and deletion of the first 11 base pairs of exon 11.

29. The method of claim 28, wherein the mutation in the gene encoding a beta-glucocerebrosidase comprises N370S.

30. The method of claim 28, wherein the mutation in the gene encoding a beta-glucocerebrosidase comprises L444P.

31. The method of claim 28, wherein the mutation in the gene encoding a beta-glucocerebrosidase comprises E326K.

* * * * *